US012033755B2

(12) United States Patent
Winkel et al.

(10) Patent No.: US 12,033,755 B2
(45) Date of Patent: Jul. 9, 2024

(54) METHOD AND ARRANGEMENT FOR IDENTIFYING SIMILAR PRE-STORED MEDICAL DATASETS

(71) Applicant: SIEMENS HEALTHINEERS AG, Forchheim (DE)

(72) Inventors: David Jean Winkel, Basel (CH); Bin Lou, Princeton Junction, NJ (US); Dorin Comaniciu, Princeton Junction, NJ (US); Ali Kamen, Skillman, NJ (US)

(73) Assignee: Siemens Healthineers AG, Forchheim (DE)

( * ) Notice: Subject to any disclaimer, the term of this patent is extended or adjusted under 35 U.S.C. 154(b) by 540 days.

(21) Appl. No.: 17/198,318

(22) Filed: Mar. 11, 2021

(65) Prior Publication Data
US 2021/0407674 A1    Dec. 30, 2021

(30) Foreign Application Priority Data

Jun. 26, 2020   (DE) .......................... 102020207943.9

(51) Int. Cl.
*G16H 50/20* (2018.01)
*G16H 10/40* (2018.01)
*G16H 20/30* (2018.01)
*G16H 30/00* (2018.01)

(52) U.S. Cl.
CPC ............. *G16H 50/20* (2018.01); *G16H 10/40* (2018.01); *G16H 20/30* (2018.01); *G16H 30/00* (2018.01)

(58) Field of Classification Search
None
See application file for complete search history.

(56) References Cited

U.S. PATENT DOCUMENTS

| 2002/0016539 | A1  | 2/2002  | Michaelis et al. |
| 2004/0247166 | A1  | 12/2004 | Giger et al. |
| 2014/0324469 | A1* | 10/2014 | Reiner ................... G16H 50/70 705/3 |
| 2020/0373003 | A1* | 11/2020 | Lyman ................. A61B 5/7275 |

(Continued)

FOREIGN PATENT DOCUMENTS

DE    10021431 A1    11/2001

OTHER PUBLICATIONS

Cao, Ruiming, et al. "Joint prostate cancer detection and gleason score prediction in mp-MRI via FocalNet." IEEE transactions on medical imaging vol. 14, No. 8, Aug. 2015. pp. 1-11.

(Continued)

*Primary Examiner* — Santiago Garcia

(57) ABSTRACT

Similar pre-stored medical datasets are identified by comparison with a current case dataset. A current case dataset is provided and includes radiological data of a patient. A number of pre-stored medical datasets each including radiological data of other patients are provided. Each case dataset is evaluated according to a predefined AI-based method to obtain a number of definitive features for that case dataset. The definitive features of the current case dataset are compared with the definitive features of each pre-stored medical dataset to identify a number of pre-stored medical datasets most similar to the current case dataset. The identified number of most similar pre-stored medical datasets are output.

13 Claims, 5 Drawing Sheets

(56) References Cited

U.S. PATENT DOCUMENTS

| | | | | |
|---|---|---|---|---|
| 2021/0366106 A1* | 11/2021 | Yao | ........................ | G16H 50/70 |
| 2022/0005222 A1* | 1/2022 | Tanikawa | .................. | A61B 6/14 |
| 2022/0413074 A1* | 12/2022 | Nehrke | .................. | G06N 3/084 |
| 2023/0098785 A1* | 3/2023 | St. Pierre | ............... | G16H 30/40 |
| | | | | 600/424 |
| 2023/0105799 A1* | 4/2023 | Nishide | .................. | A61B 5/055 |
| | | | | 382/131 |
| 2023/0237649 A1* | 7/2023 | Dillman | ................. | G16H 50/20 |
| | | | | 382/128 |

OTHER PUBLICATIONS

Litjens, Geert, et al. "Computer-aided detection of prostate cancer in MRI." IEEE transactions on medical imaging 33.5 (2014): 1083-1092.

Lou, Bin, et al. "An image-based deep learning framework for individualising radiotherapy dose: a retrospective analysis of outcome prediction." The Lancet Digital Health 1.3 (2019): e136-e147.

Rosenkrantz, Andrew B., et al. "Interobserver reproducibility of the PI-RADS version 2 lexicon: a multicenter study of six experienced prostate radiologists." Radiology 280.3 (2016): 793-804.

Yu, Xin, et al. "Deep Attentive Panoptic Model for Prostate Cancer Detection Using Biparametric MRI Scans." International Conference on Medical Image Computing and Computer-Assisted Intervention. Springer, Cham, 2020.

Yu, Xin, et al. "False positive reduction using multiscale contextual features for prostate cancer detection in multi-parametric MRI scans." 2020 IEEE 17th International Symposium on Biomedical Imaging (ISBI). IEEE, 2020. pp. 1-5.

* cited by examiner

METHOD AND ARRANGEMENT FOR IDENTIFYING SIMILAR PRE-STORED MEDICAL DATASETS

RELATED APPLICATION

This application claims the benefit of DE 102020207943.9, filed on Jun. 26, 2020, which is hereby incorporated by reference in its entirety.

FIELD

The present embodiments describe a method and arrangement for identifying similar pre-stored medical datasets, especially for comparison with a current case dataset, which includes radiological data, particularly of a tissue abnormality.

BACKGROUND

Prostate cancer is the most common cancer in men in developed countries. For more than a decade, magnetic resonance imaging (MRI) has been used to detect, precisely localize, and stage prostate cancer. As a response to the growing importance of a noninvasive assessment of the prostate gland using magnetic resonance imaging and the need to distinguish between benign processes and prostate cancer based on image features, the Prostate Imaging—Reporting and Data System (PI-RADS) was introduced in 2012. This reporting system serves to improve "the detection of clinically significant cancer." The definition of clinically significant (sPC) and insignificant prostate cancer (inPC) is based on the histological Gleason score, which reflects the tumor aggressiveness on an ordinal scale and serves as the ground-truth in all prostate cancer studies.

Multiple attempts have been made in the past to validate the PI-RADS scoring system. The findings of these studies revealed one key limitation of the PI-RADS v2 assessment score, the false positive rate lowers the cancer detection. In summary, PI-RADS category 5 lesions are assumed very likely and PI-RADS category 4 lesions are assumed to likely contain sPC while PI-RADS category 3 lesions are considered to equivocally contain sPC. Clinical trials such as PRECISION and MRI-FIRST evaluated the performance of MRI targeted prostate biopsies and could demonstrate an improved detection of sPC.

The PI-RADS score in theory equals a probability score for the detection of sPC based on the image findings. This turns out to be true for PI-RADS 5 lesions with detection rates of sPC of over 90%. For PI-RADS 4 lesions though, the detection rates of sPC after biopsy range between 22% and 60%. For PI-RADS 3 lesions, sPC is found in 12% of the cases or even not at all. Therefore, the PI-RADS scoring system has limited capabilities in the differentiation of sPC and inPC.

Although the use of the PI-RADS scoring system allows a certain standardization of prostate MRI examinations, the interpretation is a difficult task due to heterogeneous signal changes from benign prostatic hyperplasia, inflammation, and scarring after biopsy mimicking or hiding the appearance of prostate cancer. Due to these overlapping image features, only a high level of expertise required for accurate interpretation can limit the interobserver variability.

The interobserver variability is determined by the different results of an investigation or observation procedure when using different observers. It is a measure of the dependence of a clinical examination procedure on the person of the observer. If the variability is high, the sensitivity of the procedure and the specificity of the findings are strongly dependent on the examiner.

The two outlined problems (imperfect correlation between PI-RADS and Gleason scores and high interobserver variability) have so far been addressed by the use of computer-aided diagnosis (CAD) systems. Usually, the steps using a CAD system for cancer diagnosis are the following: lesion detection and lesion characterization.

However, urologists might need more information to decide on whether the patient should be biopsied or not. The second problem, the high interobserver variability, has not yet been specifically addressed.

SUMMARY

It is an object to reduce interobserver variability in evaluation of radiological data of a patient, in particular, in the assessment of prostate lesions based on MRI data.

This object may be achieved by the methods, the arrangements; and the magnetic resonance imaging systems of the claims.

According to one embodiment, a method for identifying similar pre-stored medical datasets for comparison with a current case (medical) dataset includes the following acts:
  providing a current case dataset including radiological data of a patient;
  providing a number of pre-stored medical datasets each including radiological data of a patient;
  evaluating each case dataset according to a predefined AI-based method to obtain a number of definitive features for that case dataset;
  comparing the definitive features of the current case dataset with the definitive features of each pre-stored medical dataset to identify a number of pre-stored medical datasets most similar to the current case dataset; and
  outputting the identified number of most similar pre-stored medical datasets.

The present embodiments generally relate to comparison of radiological data, i.e. medical images from the inside of a patient. Embodiments of the present embodiments are described herein to give a visual understanding of methods for comparison in medical images. A digital image is often composed of digital representations of one or more objects (or shapes). The digital representation of an object is often described herein in terms of identifying and manipulating the objects. Such manipulations are virtual manipulations typically accomplished in the memory or other circuitry/hardware of a computer system. Accordingly, is to be understood that embodiments of the present embodiments may be performed within a computer system using data stored within the computer system.

The case datasets include radiological data. In a simple embodiment, the radiological data may have the form of a pre-evaluated risk factor based on radiological data, such as e.g. the PI-RADS value. Preferably, the radiological data includes magnetic resonance imaging (MRI) images. However, it should be understood that the case datasets may include medical images of any suitable modality, such as, e.g., multi-parametric MRI (mpMRI), DynaCT, x-ray, ultrasound (US), single-photon emission computed tomography (SPECT), positron emission tomography (PET), etc. The medical image may be of any suitable dimensionality, such as, e.g., 2D (e.g., a 2D slice of an MRI image), 2.5D, or 3D.

Furthermore, the case datasets may include additional patient data, such as patient age, patient size PSA values, other data, in particular, from an electronic health report (EHR).

The general term "case datasets" includes the current case dataset, i.e. the current medical dataset or the current case medical dataset, as well as the pre-stored medical datasets. "A number of" means at least one, but preferably several or "a multitude of." The current case dataset is the input dataset, which is to be assessed by an observer. The current case dataset can be directly obtained from an imaging modality used to acquire the medical image or retrieved from a data storage, e.g. a local data memory or network data storage such as the PACS (Picture Archiving and Communication System) or a remote computer.

The pre-stored medical datasets stem from different cases, i.e. different patients, other than the current case. They are, for example, provided by local data storage or by a network data storage such as a cloud data storage. Thus, the pre-stored medical datasets are retrievable stock case datasets.

All of the datasets are evaluated and, in particular, quantified in definitive features by the same AI-based method, which renders the analyzed features directly comparable. Thus, the definitive features are defined evaluated features that are the output by the AI-based method. The quantification may also include a weighting of the definitive features in their mutual relation. In a simple embodiment, only one definitive feature is evaluated. Preferably, the definitive features and the number of definitive features are chosen in a way that allows the most distinctive comparison.

The term "AI-based method" means a machine method that mimics cognitive functions associated with the human mind. The term includes e.g. machine learning and deep machine learning.

Depending on the AI-based method, the features that are evaluated can be defined before or in the process of designing, i.e. training, the AI-based method. Therefore, the definitive features can be concrete or derived (especially with respect to mpMRI images). This means the features can have the form of human-recognizable features, such as e.g. size or shape of an abnormality; or result from more complex, human-unrecognizable connections that are implemented in the trained AI-based method. The evaluation of the definitive features is performed in particular with regard to the potential clinical significance of the data.

Due to the quantification of the obtained definitive features, it is possible to determine a distance between the features of the compared datasets and, thus, between the datasets as a whole. The distance is in an inverse relation to the similarity. It may be measured in any suitable distance measure, such as e.g. Euclidean distance.

"Identifying" means determining the most similar datasets. These can be selected and output, i.e. they are e.g. stored, transmitted or displayed. The number of the similar pre-stored medical datasets to be selected can be chosen by the observer. To facilitate the assessment of the datasets, i.e. particularly the radiological images, the identified similar pre-stored medical datasets are preferably displayed for the observer next to the current case dataset. This advantageously reduces the interobserver variability.

According to one embodiment, a dataset evaluation arrangement for identifying similar pre-stored medical datasets for comparison with a current case dataset includes
 a first interface for receiving a current case dataset including radiological data of a patient;
 a second interface to a number of pre-stored medical datasets each including radiological data of other patients;
 an evaluation processor for evaluating each case datasets according to a predefined AI-based method to obtain a number of definitive features for that case dataset;
 a comparator for comparing the definitive features of the current case dataset with the definitive features of each pre-stored medical dataset to identify a number of pre-stored medical datasets most similar to the current case dataset); and
 an output interface for outputting the identified number of most similar pre-stored medical datasets.

Thus, the dataset evaluation arrangement includes all means and is configured to realize the method for identifying similar pre-stored medical datasets. The first interface, the second interface and the output interface may be configured as separate interfaces or one or more of them may be configured as one integrated interface.

According to one embodiment, a medical display arrangement includes an arrangement for identifying similar pre-stored medical datasets and a display for displaying the identified datasets. The medical display arrangement or the arrangement for identifying similar pre-stored medical datasets does not diagnose, but provides the display for diagnosis by an observer.

According to one embodiment, a magnetic resonance imaging system includes an MRI device and a medical display arrangement or an arrangement for identifying similar pre-stored medical datasets.

Some units or modules of the dataset evaluation arrangement mentioned above can be completely or partially realized as software modules running on a processor of a computing system or a medical diagnostic arrangement. A realization largely in the form of software modules can have the advantage that applications already installed on an existing system can be updated, with relatively little effort, to install and run these units of the present application. The object is also achieved by a computer program product with a computer program that is directly loadable into the memory of a computing system or of a magnetic resonance imaging system, and which includes program units to perform the acts of the method when the program is executed by the medical diagnostic arrangement or the computing system. In addition to the computer program, such a computer program product can also include further parts such as documentation and/or additional components, also hardware components such as a hardware key (dongle etc.) to facilitate access to the software.

A non-transitory computer readable medium such as a memory stick, a hard-disk or other transportable or permanently-installed carrier can serve to transport and/or to store the executable parts of the computer program product so that these can be read by a processor of a medical diagnostic arrangement or a computing system. A processor can include one or more microprocessors or their equivalents.

Particularly advantageous embodiments and features are given by the dependent claims, as revealed in the following description. Features of different claim categories may be combined as appropriate to give further embodiments not described herein.

Generally, the present embodiments may be applied to identify similar datasets for any type of abnormality (e.g., fractures, bleeding, etc.), located on any anatomical structure (e.g., breast lungs, kidney, brain, spinal cord, etc.). The embodiments may be applied to any type of abnormality located on any type of tissue or structure in any type of radiological dataset. Apart from the prostate lesions described in detail, the embodiments are, for example easily applicable to lesions in a breast. Thus, the datasets are preferably evaluated with respect to tissue abnormalities, more preferably lesions, even more preferably indications of prostate cancer.

The evaluation of the definitive features of the pre-stored medical datasets is preferably performed in advance. This means the evaluated definitive features are stored and provided with the pre-stored medical datasets. Thus, the pre-stored medical datasets only need to be evaluated once and can then, advantageously, be compared to a plurality of current case datasets.

The AI-based method is preferably a machine learning method, more preferably a deep machine learning method. In general, machine learning enables the machine to adapt to new circumstances and to detect and extrapolate patterns. "Simple" or "traditional" machine learning methods include e.g. logistic regression, support vector machine (SVM), random forest or the like. Deep machine learning will be described in more detail later.

Preferably, histological information, e.g. the Gleason score, associated with each training dataset serves as ground truth for training the AI-based method. Using histological information and not only the PI-RADS score assessed by a clinician from radiological data allows for much more profound training with respect to clinical significance. This is because the statistical intervals on which the PI-RADS score is based are avoided.

As described before, the radiological data can be given as radiological risk score (PI-RADS value), but preferably each dataset includes radiological image data and more preferably multi-parametric MRI data.

Thus, the case datasets preferably include image data of any suitable modality, such as, e.g., multi-parametric MRI (mpMRI), DynaCT, x-ray, ultrasound (US), single-photon emission computed tomography (SPECT), positron emission tomography (PET), etc. The image data may be of any suitable dimensionality, such as, e.g., 2D (e.g., a 2D slice of an MRI image), 2.5D, or 3D.

A multi-parametric MRI mpMRI image includes a plurality of MR images acquired with different acquisition protocols. The plurality of images of mpMRI image may include T2 weighted (T2W) image, diffusion weighted imaging (DWI) with High B-value (HiB) image, and DWI apparent diffusion coefficient (ADC) image. In some embodiments, additionally or alternatively to mpMRI image, the case datasets may include dynamic contrast enhanced (DCE) sequences which depict wash-in and wash-out of certain contrast agents through various tissue compartments. Early or late enhancement as expressed in the image sequences is an important feature for abnormality detection.

Preferably, each dataset includes values of one or more of the following parameters: PSA value, PSA density, DRU score, EPE score, lymph node status and/or patient age.

PSA value means prostate-specific antigen value. The PSA density is the PSA value divided by the prostate volume. DRU means a digital rectal exam. DRU has a kind of staging system where higher scores (with PSA and the histopathology) increase the risk of biochemical recurrence. EPE means extra prostatic extension, i.e. meaning tumor is growing beyond the capsule. The result of the DRU score, EPE score and Lymph node status may have a binary form, such as positive (1) or negative (0), or even be quantified on a scale by a clinician.

These values can, for example, be obtained via an EHR or entered by a clinician. The values are known for their significance in assessing the risk of prostate cancer and, thus, provide relevant criteria for the comparison of the datasets.

Each dataset includes preferably values of one or more of the following radiologically determined parameters: PI-RADS value, lesion size, lesion location and/or organ volume. A clinician or radiologist typically determines the PI-RADS value. The other parameters can, for example, be obtained with an established CAD algorithm and then be evaluated with the predefined AI-based method. However, a lesion that has been detected and/or segmented by a CAD algorithm does not in itself provide immediate information regarding the risk of malignancy or clinical significance.

In a simple preferred embodiment, the predefined AI-based method evaluates the dataset to obtain a single scalar value for a risk score as definitive feature. This greatly facilitates the comparison between the definitive feature of the current case dataset and the pre-stored medical dataset. However, a more profound comparison is based on more than a single scalar value as described below.

Preferably, the predefined AI-based method evaluates the dataset to obtain a vector of definitive features including values for one or more of the following radiomic parameters or parameter groups: lesion size, lesion intensity, lesion shape, lesion texture, and wavelet transformation Wavelet transformation gives a vector of features, not a just scalar. Also the term "lesion intensity" describes a group of features (i.e. vector). The vector of definitive features may preferably include one or both of these groups of parameters (vectors). For example, lesion intensity features could include average intensity of the images, maximum intensity, variance of intensity and so on. Lesion intensity, lesion shape, lesion texture, wavelet transformation are general categories of features. With respect to the extraction and evaluation of radiomic features, "B. Lou et al, An image-based deep learning framework for individualizing radiotherapy dose: a retrospective analysis of outcome prediction, The Lancet Digital Health 2019" is incorporated by reference into the current description.

Further preferred definitive features include the intensity of various contrasts within the candidate lesion, a variance or other higher order statistical calculation of intensities within the candidate lesion, various radiomic features within the candidate lesion, and various lexicon based features computed within the candidate lesion by following standards or common domain knowledge established within the community. For example, regarding prostate lesions, lexicon based features could be computed following the Prostate Imaging Reporting and Data System (PI-RADS).

Alternatively, based on one or more of the above features, the machine learning method is preferably trained to compute 1) a clinical relevance map for lesions to increase the detection rate, and 2) a label to further ratify whether the candidate lesion is positive (i.e., clinically significant) or not to reduce the false positive rate of the system.

The clinical relevance map or heat map is similar to a probability map that is specific to one or more chosen lexicon based features (i.e., the input lexicon based feature) or a nonlinear combination of lexicon based features (learned through a machine learning algorithm). Computation of the lexicon based features, such as, e.g., the PI-RADS lexicon for prostate lesions, may be performed based on candidate lesion shape and underlying intensities in various contrasts. The lesion shape is determined based on attributes computed for round, oval, lenticular, lobulated, water drop shaped, wedge shaped, linear, and irregular shapes. The lesion margin is computed based on attributes of the lesion border, such as, e.g., various contrasts, circumscribed, non-circumscribed, irregular, speculated, hyper/hypo intense, organized chaos (non-homogenous), and erased charcoal sign. In one embodiment, the lexicon based features (e.g., hypo/hyper intense) could be implemented using image processing filters and combined together using an additional network, through a logistic regression, or using similar models. In one embodiment, a similar machine learning method may be trained and applied to evaluate the definitive features of the dataset.

The predefined AI-based method evaluates the dataset to obtain a vector of defined features including one or more values for a risk score and values for parameters of a task-specific fingerprint. The risk score is a predicted value for the clinical significance, such as e.g. a predicted Gleason score. The task-specific fingerprint differs from classical radiomics features in that it does not include generic measurements and is trained to be most discriminative for pathology results. This method extracts higher-dimensional definitive features, particularly from mpMRI data, that cannot be fully captured by pre-defined hand-crafted features. This multi-task method stratifies the datasets in different groups based on the risk score and adds constraints to the definitive features, so that also the physical properties of the lesion are closely related. For this purpose, preferably, a deep learning method is used as the predefined AI-based method.

The expression "deep learning" here refers to a method, an arrangement or software module based on deep (machine) learning. Deep learning is a special method of machine learning that is based on an artificial neural network with representation learning. Preferred deep learning networks are deep neural networks, deep belief networks, recurrent neural networks and convolutional neural networks. The term "network" indicates here that there could be a physical network, i.e. a network of physical nodes connected by signal lines (e.g. a FPGA or a network of physical computing devices). However, the term also means that there could be a virtual network based on virtual nodes (e.g. virtual neurons) connected by virtual signal lines (e.g. nodes linked with each other). Thus, the deep learning network could be present as physical (hardware) network in the form of a hardware module or as a virtual network in form of a software module, wherein the software module can be present in an individual (hardware) computing module.

In the case of a virtual network, there are often artificial neurons present as elementary units in the network. An artificial neuron is a mathematical function conceived as a model of a biological neuron, receiving one or more inputs that could e.g. represent excitatory postsynaptic potentials and inhibitory postsynaptic potentials at neural dendrites, and sums them to produce an output. Usually each input is separately weighted, and the sum is passed through a non-linear function known as an "activation function" (or "transfer function"). A preferred activation function has a sigmoid shape, but it may also take the form of other non-linear functions, piecewise linear functions, or step functions.

The deep learning network may have a well-known basic architecture. However, its inner structure and its performance is individually shaped after the training. Thus, it can be said that the training defines the inner "structure" of the deep learning network and distinguishes it from other trained deep learning networks (even of the same basic architecture).

Within its training phase, the weights or parameters within its structure are automatically adjusted to evaluate the definitive features for the radiological datasets with respect to their clinical significance.

The deep learning network has preferably been trained with multiple (preferably more than a thousand) training-datasets based on mpMRI datasets including tissue abnormalities, in preferably prostate lesions, and histological information, preferably the Gleason score evaluated by clinicians. The training is performed by entering the training-datasets into an input layer of the deep learning network; calculating a loss-value for each training-dataset based on the difference between the output of the deep learning network and the histological information; and adjusting parameters of the deep learning network until the loss-value is minimized.

Using these labels as ground-truth data, a deep learning network can be trained, with the previously described inputs and outputs. Architecture of such a network can include e.g. alternating convolutional and pooling layers, for the output layer e.g. a Sigmoid function can be used for the classification set-up. The convolutional layers extract the definitive features, pooling layers reduce the dimensionality. Thus, the neural network is designed as an encoder-decoder network, such as e.g., VGG-16 or ResNet to increase performance.

For the optimization of the weights/parameters of all layers, well-known optimization approaches, e.g. the Gradient Descent or Adam in combination with e.g. the cross entropy loss function, can be used.

After the training, the weights/parameters of the network are adapted for the specific task and can e.g. evaluate the definitive features from previously unseen continuous measurements.

The utilization of this neural network would eliminate the need of post-processing the data with hand-crafted features and a priori knowledge. Furthermore, the processing with a deep neural network is very fast (e.g. in the range of milliseconds for one forward pass).

Thus, the predefined AI-based method is preferably a convolutional neural network configured to evaluate datasets to obtain a vector of definitive abstract features.

The most similar pre-stored medical datasets are preferably identified by minimum distance measures between the datasets. For this purpose any suited distance measure may be used, for example the Euclidian distance $$D(x_i, y_j) = |x_i - y_j|_2 \qquad \text{Eq. (1);}$$

the Cosine Similarity $$D(x_i, y_j) = x_i * y_j / (|x_i| |y_j|) \qquad \text{Eq. (2);}$$

or the Mahalanobis Distance $$D(x_i, y_j) = (x_i - y_j) * M * (x_i - y_j) \qquad \text{Eq. (3),}$$

wherein $x_i$ denotes the vector of definitive features for the current case dataset, $y_j$ denotes the vector of definitive features for the compared pre-stored medical dataset, $D(x_i, y_j)$ is the calculated distance measure and M is the covariance matrix of the training datasets.

Preferably, the current case dataset and the identified similar pre-stored medical datasets are output, i.e. they are stored, transmitted or displayed. More preferably, the datasets are displayed with an overlaid heat map indicating the clinical significance of the respective regions. In this way, a "virtual biopsy" can be performed. If displayed together, the datasets advantageously simplify the assessment of the current case dataset for an observer, since he can immediately compare the current case to the most similar cases, for which histological findings are known.

The components of the dataset evaluation arrangement are part of a data-network, wherein preferably the data-network and a magnetic resonance imaging system which provides image data are in data-communication with each other, wherein the data-network preferably includes parts of the internet and/or a cloud-based computing system, wherein preferably the device according to the invention or at least the deep learning network is realized in this cloud-based computing system. For example, the components of the device are part of a data-network, wherein preferably the data-network and a medical imaging system which provides the image data are in communication with each other. Such a networked solution could be implemented via an internet platform and/or in a cloud-based computing system.

The method may also preferably include elements of "cloud computing." In the technical field of "cloud computing," an IT infrastructure is provided over a data-network, e.g. a storage space or processing power and/or application software. The communication between the user and the "cloud" is achieved by means of data interfaces and/or data transmission protocols.

Provision of data preferably takes place via a data channel (for example a data-network) to a "cloud." This "cloud" includes a (remote) computing system, e.g. a computer cluster that typically does not include the user's local machine. This cloud can be made available in particular by the medical facility, which also provides the medical imaging systems. In particular, the image acquisition data is sent to a (remote) computer system (the "cloud") via an RIS (Radiology Information System) or a PACS (Picture Archiving and Communication System).

The above-mentioned units, especially the deep learning network, are preferably present on the "cloud" side. A preferred dataset evaluation arrangement further includes, a local computing unit connected to the device via a data channel (e.g. a data-network, particularly configured as RIS, PACS, PI-RADS, BI-RADS). The local computing unit includes at least one data receiving interface to receive data. Moreover, it is preferred if the local computer additionally has a transmission interface in order to send data to the device.

Preferably, the plurality of the mpMR images may be preprocessed to address or remove variability or variances between the plurality of images before being evaluated by a dataset evaluation arrangement. Removing variances between the plurality of the mpMR images ensures a high level of performance even with limited data availability. Such variances may include geometric variances, intensity variances, variances in the ground truth preparation, or any other variance.

Geometric variability is preferably addressed to properly align the plurality of images of mpMR image for accurate and efficient reading. In particular, a registration act is performed to align the plurality of images of mpMR image. In addition, to obtain uniform dimensionality and voxel spacing of the images across modalities and patient cases, each image is preferably transformed to a space with identical dimensions and spacings (e.g., 15×15×9 cm and 0.5×0.5×3 mm/pixel, respectively). A prostate segmentation algorithm is preferably performed to center the images around the prostate (or any other object of interest). Thus, by removing geometric variability, each of the plurality of images of mpMR image will have the same size, orientation, spacing, and position properties.

To ensure a consistent intensity distribution across patient cases for the different datasets of mpMR image, various forms of normalization computations are preferably performed. First, the DWI images are interpolated to a common b-value (e.g., 2000) to ensure comparable intensities. The b-value is a factor that reflects the strength and the timing of the gradients used to generate diffusion-weighted images. In one embodiment, such DWI images are normalized according to an anatomical intensity range computed based on low b-value images. In one embodiment, a low b-value is a b-value less than 100 s/mm2, and preferably a b-value of 0. Additionally, a KTrans parametric map is computed from dynamic contrast enhanced (DCE) images with fixed model parameter values. The KTrans is computed based on a T1-weighted DCE sequence to represent the tissue permeability. Tissue permeability, along with early or late enhancement of contrast, is informative in detecting and characterizing an abnormality. The T2W images may be standardized based on the intensities of referencing tissues such as fat or muscle. The identification of referencing tissues may be performed using landmark detection models. To further ensure intensity comparability across patient cases of different modalities, the images are normalized. The normalization may be based on a median, average, or any other statistically robust metric, such as, e.g., an average of the middle two quartiles of an intensity histogram.

BRIEF DESCRIPTION OF THE DRAWINGS

Other objects and features of the present embodiments will become apparent from the following detailed descriptions considered in conjunction with the accompanying drawings. It is to be understood, however, that the drawings are designed solely for the purposes of illustration and not as a definition of the limits of the invention.

DETAILED DESCRIPTION OF THE EMBODIMENTS

Figure 1:
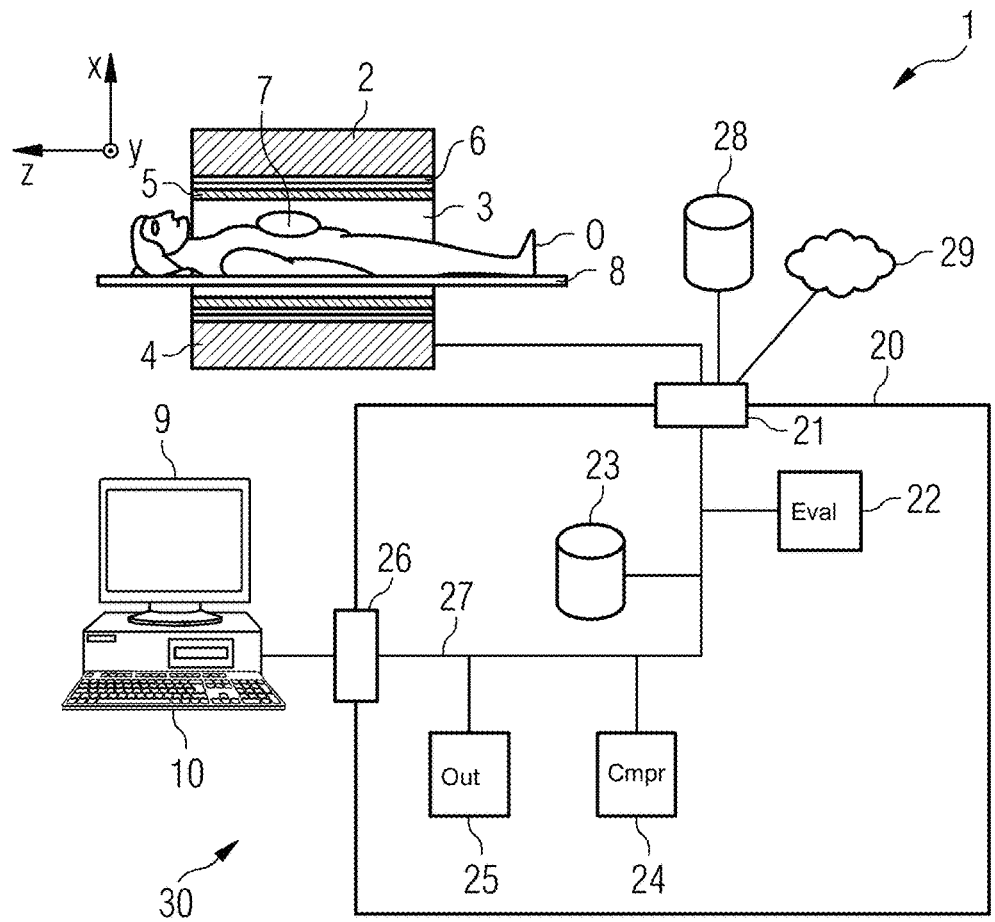
FIG. 1 shows a simplified example of an MRI system including an example of a display arrangement including an example of a dataset evaluation arrangement.

FIG. 1 shows a schematic representation of a magnetic resonance imaging system 1 ("MRI-system"). The MRI system 1 includes the actual magnetic resonance scanner (data acquisition unit) 2 with an examination space 3 or patient tunnel in which a patient or test person O is positioned on a driven bed 8, in whose body the actual examination object is located.

The magnetic resonance scanner 2 is typically equipped with a basic field magnet system 4, a gradient system 6 as well as an RF transmission antenna system 5 and an RF reception antenna system 7. In the shown exemplary embodiment, the RF transmission antenna system 5 is a whole-body coil permanently installed in the magnetic resonance scanner 2, in contrast to which the RF reception antenna system 7 is formed as local coils (symbolized here by only a single local coil) to be arranged on the patient or test subject. In principle, however, the whole-body coil can also be used as an RF reception antenna system, and the local coils can respectively be switched into different operating modes.

In general, the skilled person is familiar with the design and function of an MRI scanner. For this reason, a more detailed description is omitted.

Furthermore, the MRI system 1 includes a display arrangement 30, having a keyboard 10 for user input; a screen 9 for displaying information and data and a dataset evaluation arrangement 20. The dataset evaluation arrangement 20 is connected to the keyboard 10; the screen 9 via an input/output interface 26 and to the MRI scanner 2 via an input interface 21. The MRI scanner 2 provides mpMR image, preferably including a prostate lesion, as radiological data for the current case dataset ID. Additionally the dataset evaluation arrangement 20 is connected to an external storage 28, for example, storage of an internal hospital network or information system (RIS), from which additional patient data in from of an electronic health record (EHR) can be received and added to the current case dataset ID. A further connection is established via the input interface 21 to a cloud storage 29 that can provide pre-stored medical datasets SD1, SD2, SD3, . . . .

The dataset evaluation arrangement 20 further includes a processor operating using instructions to provide an evaluator 22 for evaluating definitive features DF of the case datasets ID, SD1, SD2, SD3, . . . ; comparator 24 the definitive features DF; and output generator 25. A data storage or memory 23 may be included for storing the definitive features DF. The components of the dataset evaluation arrangement 20 are connected via a data connection 27, that may have the form of a BUS or a network connection.

It is to be understood that the components of the MRI system 1 and/or the dataset evaluation arrangement 20 can be spatially distributed in a cloud-based system. Alternatively, the dataset evaluation arrangement 20 can be designed integrally and optionally even integrate the data storage components 28, 29 that are here depicted separately. The function of the dataset evaluation arrangement 20 is explained in more detail with respect to the method of shown FIG. 2.

Figure 2:
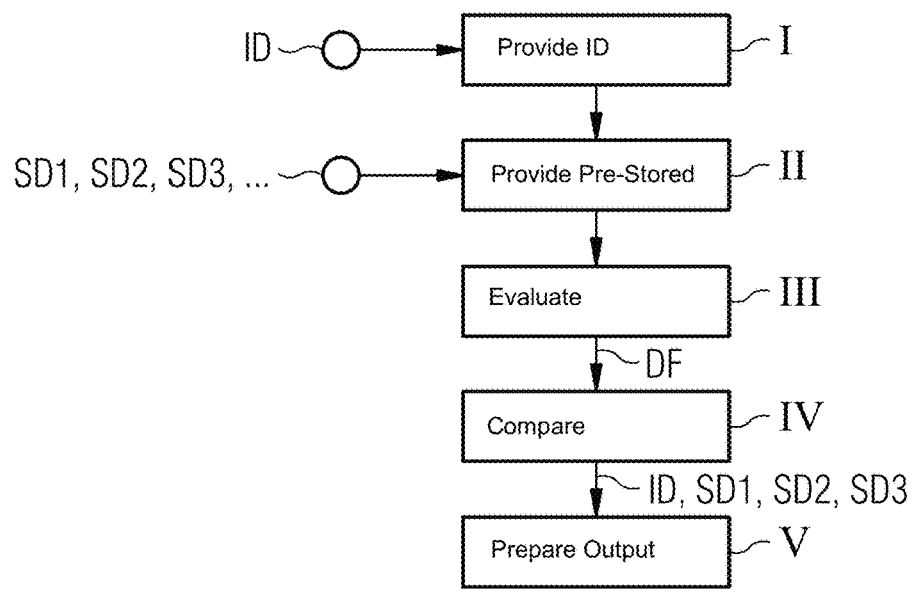
FIG. 2 shows an exemplary block diagram of a method for identifying similar pre-stored medical datasets.

FIG. 2 shows a block diagram of an exemplary embodiment of the method for identifying similar pre-stored medical datasets SD1, SD2, SD3 for comparison with a current case dataset ID.

In act I, the current case dataset ID is provided as input data by the MR scanner 2, by the internal storage 23, by the external storage 28 or by the cloud storage 29.

In act II, the pre-stored medical datasets SD1, SD2, SD3, . . . are provided by the internal storage 23, by the external storage 28 or by the cloud storage 29. The type and form of all case datasets ID, SD1, SD2, SD3, . . . are substantially the same. However they can be adjusted to each other by a post-processing process, e.g. with respect to image size, resolution, intensity, contrast etc.

In act III, each case dataset ID, SD1, SD2, SD3, . . . is evaluated with a predefined AI-based method to obtain its definitive features DF. The type and form of the input case dataset ID, SD1, SD2, SD3, . . . and of the obtained definitive features DF strongly depend on the utilized AI-based method and are described in more detail with respect to FIG. 3 to 6.

Since the pre-stored medical datasets SD1, SD2, SD3, . . . are easily retrievable, preferably evaluated in advance and their definitive features DF stored in advance, the current case dataset ID may practically be the only real input data ID for the method.

In act IV, the definitive features DF of each pre-stored medical dataset SD1, SD2, SD3, . . . are compared with the definitive features DF of the current case dataset ID. The comparison is performed with suitable distance measure e.g. according to one of the equations (1) to (3). The pre-stored medical datasets SD1, SD2, SD3 with the minimal distance to the current case dataset ID are identified as the most similar pre-stored medical datasets SD1, SD2, SD3. The number of the identified similar pre-stored medical datasets SD1, SD2, SD3 may be chosen by a user input.

In act V, the case datasets ID, SD1, SD2, SD3 are prepared for output, for example by overlaying the same respective additional data (e.g. segmentation information, heat map etc.) on each of the selected MR images. Finally, the case datasets ID, SD1, SD2, SD3 are displayed together. Due to the comparison of the similar datasets ID, SD1, SD2, SD3 an observer can make a more profound assessment of the risk or clinical significance. Thus, the interobserver variability can be reduced by the inventive method.

Figure 3:
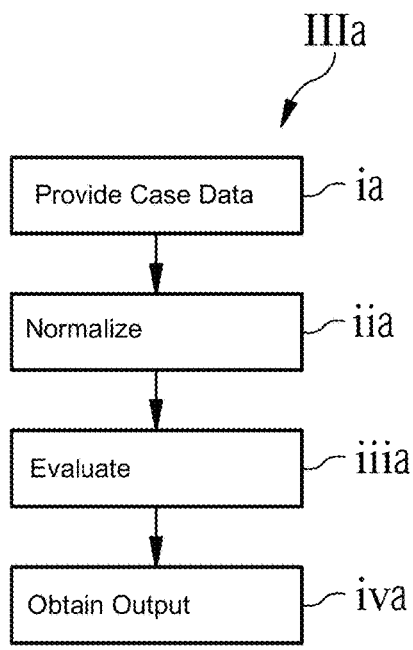
FIG. 3 shows a first exemplary block diagram of details of act III of the method of FIG. 2.

FIG. 3 shows a block diagram of a first embodiment IIIa of act III of the inventive method.

In act ia, a case dataset is provided as input data which includes a PI-RADS value, lesion size and/or lesion location as radiological data. A radiologist can evaluate these radiological parameters in advance. Alternatively, lesion size and/or lesion location can be obtained via a CAD algorithm. In addition, the input data includes information of the EHR, such as PSA value, PSA density, patient age.

In act iia, the inputs are normalized. For example, the lesion size can be adjusted to the patient size or the like.

In act iiia, the inputs are evaluated be the method. The AI-based method can be designed, for example, as a simple machine learning method such as e.g. an SVM method.

In act iva, the output of the definitive feature DF is obtained in the form of a simple scalar value describing the risk factor of the case dataset.

The AI-based method of IIIa is trained with a fixed number of defined input variables and by minimizing the difference of the obtained risk factor to the histological assessed Gleason score, which serves as ground truth.

The same input variables as during the training are used for real application of the method after training.

In this embodiment, the distance measure for comparing the similarity of different case datasets is simply the difference between the respective risk factors which are obtained as definitive features DF.

Figure 4:
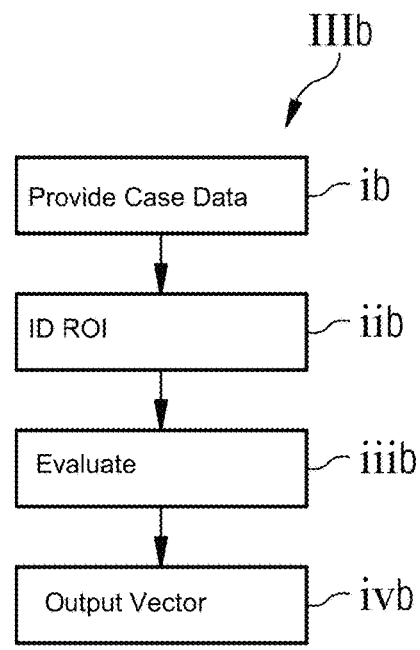
FIG. 4 shows a second exemplary block diagram of details of act III of the method of FIG. 2.

FIG. 4 shows a block diagram of a second embodiment IIIb of act III of the inventive method.

In act ib, a case dataset is provided as input data which includes an mpMR image.

In act iib, a region of interest is identified in the mpMR image and the image is segmented. This can be achieved by applying a CAD algorithm or a machine learning method trained for the purpose of lesion detection and segmentation.

In act iiib, the actual AI-based method evaluates the definitive features DF by extracting generic radiomic features from the mpMR images and a correlation analysis to select from the redundant features.

In act ivb, a vector of the (scalar) selected radiomic features is output as definitive feature DF.

The AI-based method of IIIb is trained using a ROC-Curve analysis with the histologically determined Gleason score as ground truth, wherein the extracted radiomic features can directly be used to distinguish between different Gleason score groups. The AI-based method may be designed as a random forest method. For example, cases with Gleason score (GS) larger than 6 can be considered as positive class (malignant) and GS<=6 belong to a negative class (benign). Then a binary classifier can be implemented to discriminate the two classes. Moreover, an ordinal classification can be performed, in which the probability of being each GS category, e.g. GS<=6, GS=7, GS=8, and GS>=9 can be predicted.

Figure 5:
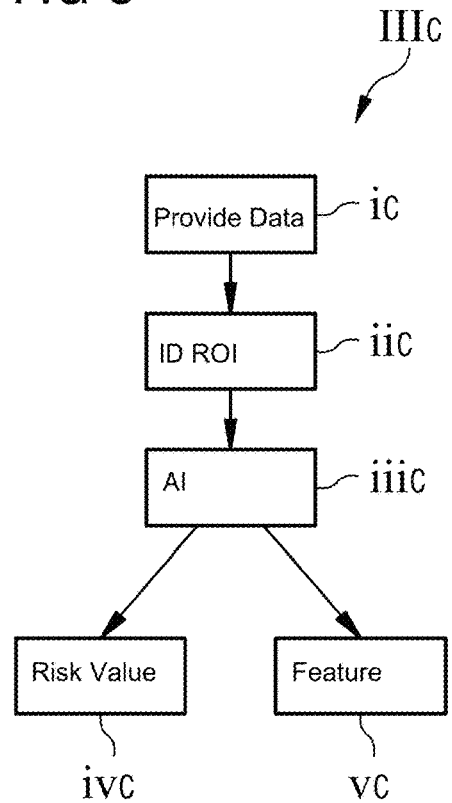
FIG. 5 shows a third exemplary block diagram of details of act III of the method of FIG. 2.

FIG. 5 shows a block diagram of a third embodiment IIIc of act III of the inventive method.

In act ic, a case dataset is provided as input data which includes an mpMR image.

In act iic, a region of interest is identified in the mpMR image and the image is segmented. This can be achieved by applying a CAD algorithm or a machine learning method trained for the purpose of lesion detection and segmentation.

In act iiic, the actual AI-based method is implemented as a decoder network with respect to decoded, abstract (non-generic) features.

In act ivc, a risk value in form of a predicted gleason score is obtained from the decoded features by a classification network as a first component of the definitive feature.

In act vc, standard radiomic features as well as a PI-RADS value are obtained from the decoded features by a decoder network as a lesion-specific fingerprint.

The lesion-specific fingerprint is used as further constraint to the otherwise under defined problem, to keep the physical properties of the lesion close to the PI-RADS.

The risk value and the lesion-specific fingerprint are output as definitive features.

The AI-based method of IIIc is trained using a ROC-Curve analysis by comparing the risk factor predicted by the AI-decoder-classification network with the histologically determined Gleason score as ground truth.

Figure 6:
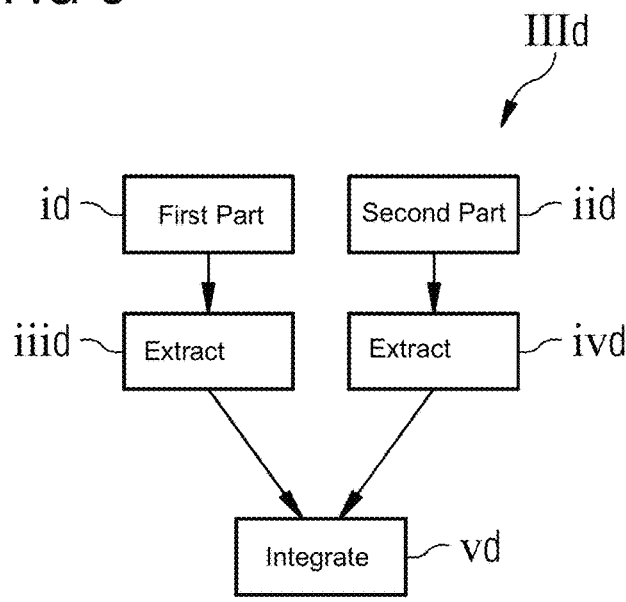
FIG. 6 shows a fourth exemplary block diagram of details of act III of the method of FIG. 2.

FIG. 6 shows a block diagram of a fourth embodiment IIId of act III of the inventive method.

Here, two subnetworks are used for the evaluation.

In act id, a first part of the case dataset, which includes an mpMR image, is provided as input data for the first subnetwork.

In act iid, a second part of the case dataset, which includes additional parameters from the EHR (as described above), is provided as input data for the second subnetwork.

In act iid, a region of interest is identified in the mpMR image and the image is segmented. This can be achieved by applying a CAD algorithm or a machine learning method trained for the purpose of lesion detection and segmentation.

In act iiid, the first subnetwork, which is designed as convolutional neural network (CNN), extracts features from the mpMR image. The convolutional neural network may be of the type of a ResNet or DenseNet.

In act ivd, the second subnetwork, which is designed as fully connected network, extracts features from the additional parameters.

In act vd, the extracted parameters of the first subnetwork and the second subnetwork are integrated into a vector which is output includes the definitive features DF as components.

The AI-based method of IIIc is trained by minimizing a triplet loss function L of the form $$L(A,P,N)=\max(D(A,P)-D(A,N)+\alpha,0) \qquad \text{Eq. 4,}$$

wherein A is the anchor lesion (reference), P is the positive example (lesion with the same histological result), and N is the negative example (lesion with different histological result). D is one of the above mentioned distance measures. Thus, the network that makes the distance between the encoding features of the anchor and positive example to be less than or equal to the distance between the encoding features of the anchor and negative example is promoted. The ground truth of the histological information is built on biopsy results. Two lesions with the same Gleason score are positive examples to each other.

In this embodiment IIId, the acts iid and ivd are optional and may be omitted. However, a more accurate result may be obtained by performing all the described acts.

Figure 7:
FIG. 7 shows an example of an MR image of a prostate as part of a current case dataset.
Figure 8:
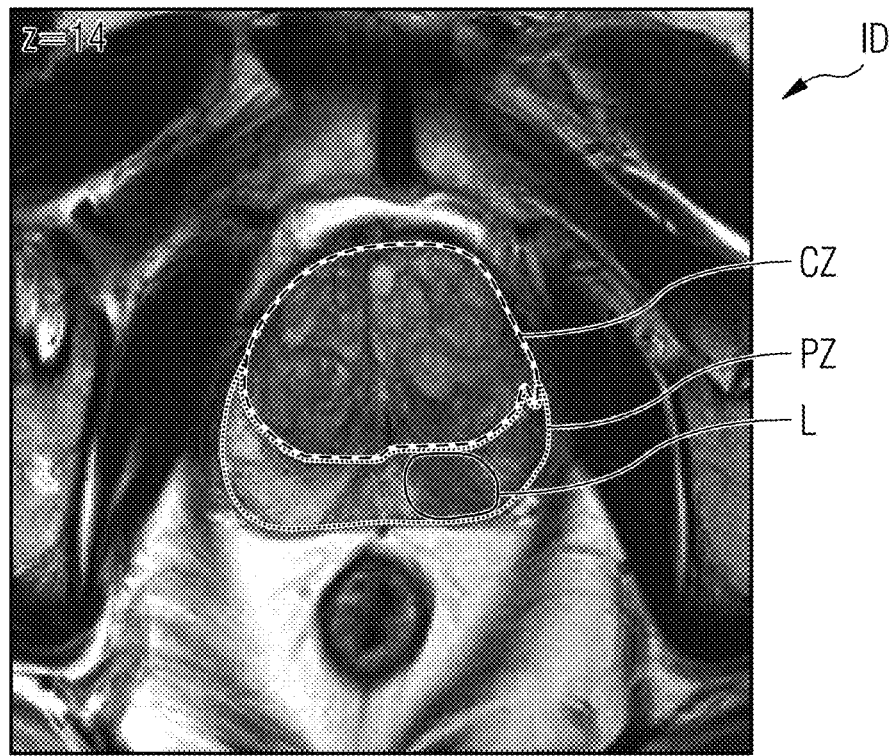
FIG. 8 shows the MR image of FIG. 7 with example indicated segments of the prostate.

FIG. 7 shows an example of an MR image of a prostate as part of a current case dataset ID. In FIG. 8, this image is depicted with indicated segments of the prostate. The segments include a central zone CZ and a peripheral zone PZ of the prostate as well as a lesion L.

Figure 9:
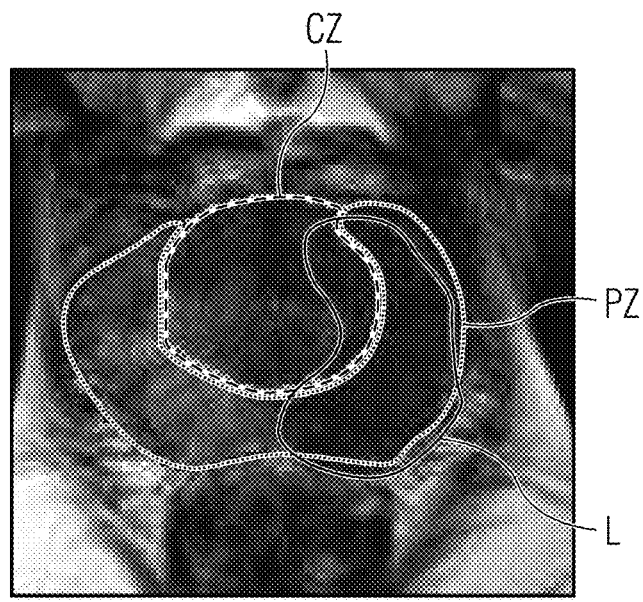
FIG. 9 shows three examples of MR images of different prostates as part of pre-stored medical datasets similar to the current case dataset.
Figure 9:
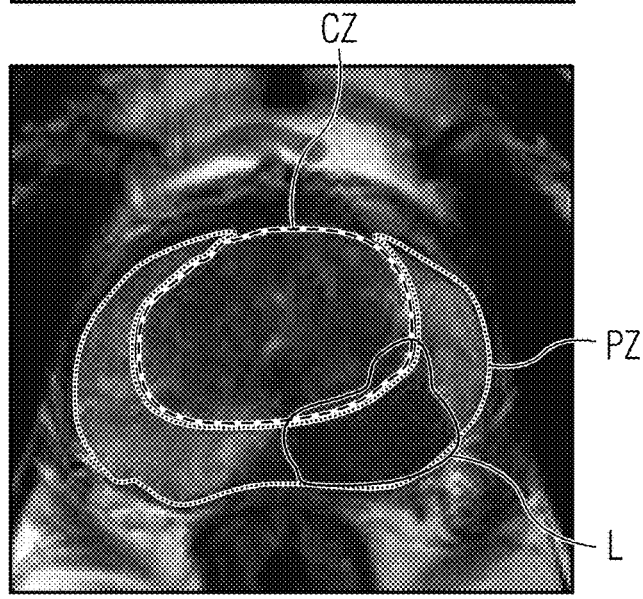
Figure 9:
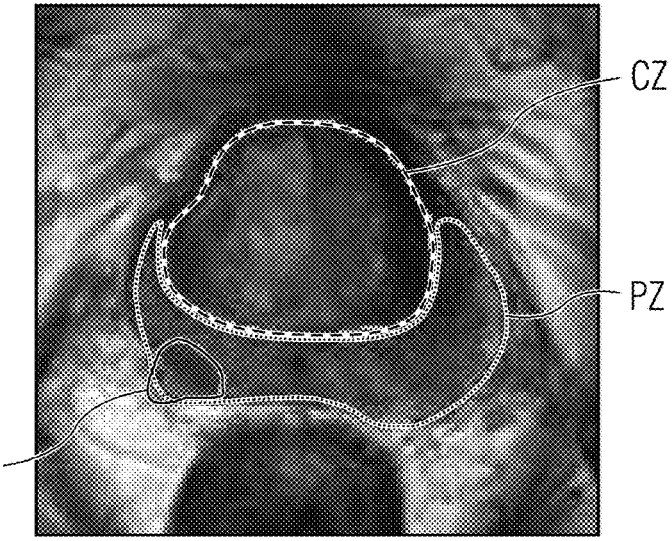

FIG. 9 shows three examples SD1, SD2, SD3 of MR images of different prostates which are a part of the pre-stored medical datasets to which the current case dataset shown in FIG. 7 and FIG. 8 is compared by the method according to one of the embodiments described above. Out of a plurality of pre-stored medical datasets SD1, SD2, SD3, . . . the pre-stored medical datasets SD1, SD2, SD3 have been identified as the three pre-stored medical datasets most similar to the current case dataset ID. Despite of the obvious differences in size and location of the lesions depicted for the pre-stored medical datasets SD1, SD2, SD3 they are identified as similar for reasons of clinical significance that might not directly be obvious for a human observer. However, thorough study of the datasets might reveal similarities in the smaller structures of the lesions or in other MR images, acquired with different parameters and/or acquisition protocols.

For an observer, it becomes easier or even possible in the first place to discover these similarities due to the method and arrangements of the invention.

Figure 10:
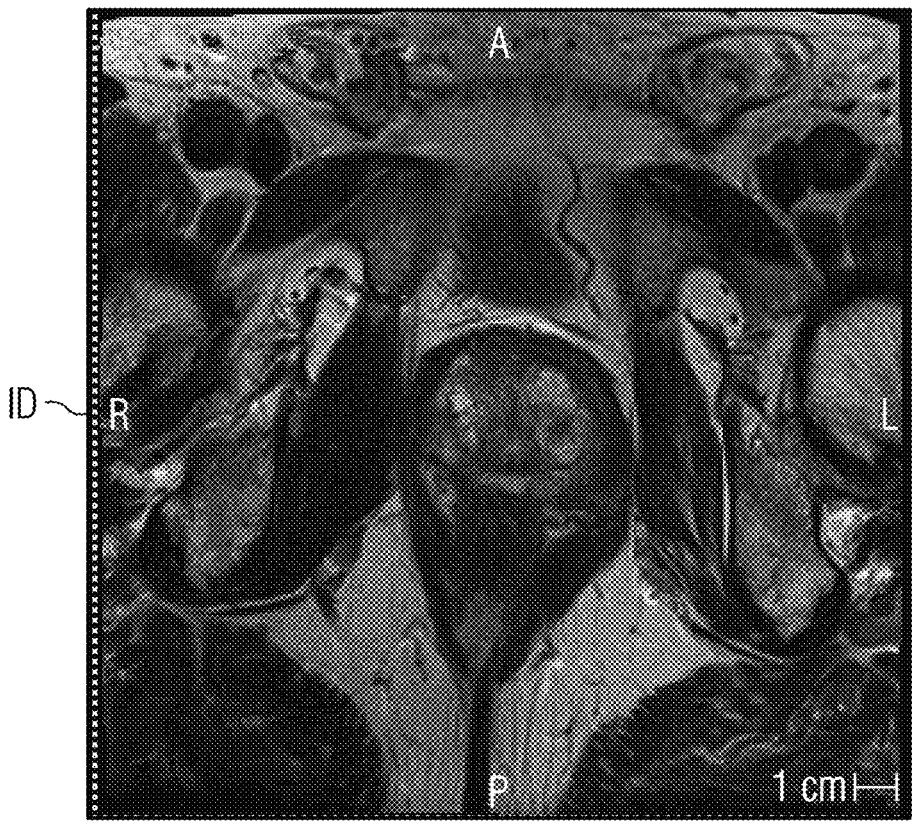
FIG. 10 shows another example of an MR image of a prostate as part of a current case dataset and an associated heat map.
Figure 10:
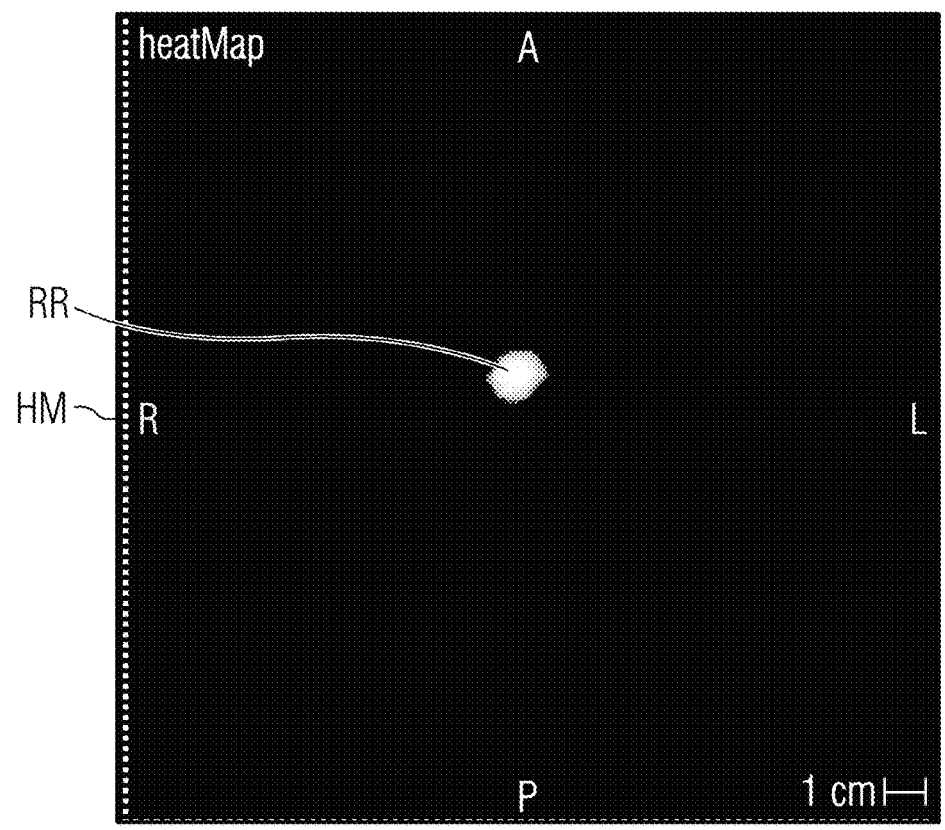

FIG. 10 shows another example of an MR image of a prostate as part of a current case dataset ID and a heat map HM that can be obtained by some embodiments of the invention (e.g. by the predefined AI-methods IIIb, IIIc and IIId). The heat map HM indicates risk regions RR in which a malign lesion is indicated with high clinical significance. The heat map can be a binary map as shown here or color coded with respect to the clinical significance. It can be displayed separately, as shown here, or overlaid on the MR image. The display of an overlaid heatmap for the current case dataset and the pre-stored medical datasets, that have been identified as most similar, can further facilitate the assessment by the observer.

Although the present invention has been disclosed in the form of preferred embodiments and variations thereon, it will be understood that numerous additional modifications and variations could be made thereto without departing from the scope of the invention. For the sake of clarity, it is to be understood that the use of "a" or "an" throughout this application does not exclude a plurality, and "comprising"

does not exclude other acts or elements. The mention of an "arrangement" or a "system" does not preclude the use of more than one unit or device and does not preclude a spatial distribution of the components e.g. in a network or a cloud system.

The invention claimed is:

1. A method for identifying similar pre-stored medical datasets for comparison with a current case dataset, the method comprising:
   providing a current case dataset comprising radiological data of a patient;
   providing a number of pre-stored medical datasets each comprising radiological data of other patients;
   obtaining features for the current case dataset and each of the number of pre-stored medical datasets based on an evaluation of the current case dataset and the number of pre-stored medical datasets according to a predefined AI-based method comprising a convolutional neural network configured to evaluate datasets to obtain a vector of definitive abstract features, the convolutional neural network trained by comparing a predicted risk factor with a histologically determined Gleason score as ground truth;
   identifying a number of pre-stored medical datasets most similar to the current case dataset based on a comparison of the features of the current case dataset with the features of each of the number of pre-stored medical datasets; and
   outputting the identified number of most similar pre-stored medical datasets.

2. The method according to claim 1, wherein obtaining comprises obtaining by the evaluation of the current case and pre-stored medical datasets with respect to tissue abnormalities.

3. The method according to claim 1, wherein each current case and pre-stored medical dataset comprises multi-parametric MRI data.

4. The method according to claim 1, wherein each current case and pre-stored medical dataset comprises values of one or more of the following parameters: PSA value, PSA density, DRU score, EPE score, lymph node status, and/or patient age.

5. The method according to claim 1, wherein each current case and pre-stored medical dataset comprises values of one or more of the following radiologically determined parameters: PI-RADS value, lesion size, lesion location and/or organ volume.

6. The method according to claim 1, wherein the predefined AI-based method obtains a single scalar value for a risk score as a feature in the evaluation of each current case and pre-stored medical dataset.

7. The method according to claim 1, wherein the predefined AI-based method obtains, as part of the evaluation, a vector of features comprising values for one or more of the following radiomic parameters: lesion size, lesion intensity, lesion shape, lesion texture, wavelet transformation.

8. The method according to claim 1, wherein the predefined AI-based method obtains, as part of the evaluation, a vector of features comprising one or more values for a risk score and values for parameters of a task-specific fingerprint.

9. The method according to claim 1, wherein the most similar pre-stored medical datasets are identified by minimum distance measures between the current case dataset and the pre-stored medical datasets.

10. The method according to claim 2, wherein obtaining comprises obtaining by the evaluation of the current case and pre-stored medical datasets with respect to tissue abnormalities comprising indications of prostate cancer.

11. An evaluation arrangement for identifying similar pre-stored medical datasets for comparison with a current case dataset, the evaluation arrangement comprising:
   a first interface for receiving a current case dataset comprising radiological data of a patient;
   a second interface to a number of pre-stored medical datasets each comprising radiological data of another patient;
   a processor operating pursuant to instructions stored in a memory, the instruction comprising instruction to:
      evaluate each current case and pre-stored medical dataset according to a predefined AI-based method to obtain a number of features for each respective case dataset, wherein the number of features comprise a vector of definitive features including values for one or more of the following radiomic parameters or parameter groups: lesion size, lesion intensity, lesion shape, lesion texture, and wavelet transformation, wherein the predefined AI-based method comprises a convolutional neural network trained by comparing a predicted risk factor with a histologically determined Gleason score as ground truth; and
      identify a number of pre-stored medical datasets most similar to the current case dataset based on a comparison of the features of the current case dataset with the features of each pre-stored medical dataset; and
   an output interface for outputting the identified number of most similar pre-stored medical datasets.

12. The evaluation arrangement of claim 11 further comprising a screen for displaying the identified datasets.

13. A non-transitory computer-readable medium on which program elements are stored that can be read and executed by a computer, the non-transitory computer-readable medium having stored thereon instructions for:
   providing a current case dataset comprising radiological data of a patient;
   providing a number of pre-stored medical datasets each comprising radiological data of other patients;
   obtaining a number of features including one or more values for a risk score and values for parameters of a task-specific fingerprint for each respective case dataset based on an evaluation of each current case and pre-stored medical dataset according to a predefined AI-based method, wherein the AI-based method comprises a convolutional neural network configured to evaluate datasets to obtain a vector of definitive abstract features, the convolutional neural network trained by comparing a predicted risk factor with a histologically determined Gleason score as ground truth;
   identifying a number of pre-stored medical datasets most similar to the current case dataset based on a comparison of the features of the current case dataset with the features of each pre-stored medical dataset; and
   outputting the identified number of most similar pre-stored medical datasets.

* * * * *